(12) United States Patent
Zanon

(10) Patent No.: US 8,508,163 B2
(45) Date of Patent: Aug. 13, 2013

(54) OPERATING DEVICE PREFERABLY FOR MACHINES FOR CONTROLLING AND INSPECTING CONTAINERS AND/OR THEIR CONTENTS, AND CORRESPONDING MACHINE

(76) Inventor: Massimiliano Zanon, Monticello Conte Otto (IT)

(*) Notice: Subject to any disclaimer, the term of this patent is extended or adjusted under 35 U.S.C. 154(b) by 628 days.

(21) Appl. No.: 12/744,889

(22) PCT Filed: Nov. 27, 2007

(86) PCT No.: PCT/IT2007/000827
§ 371 (c)(1),
(2), (4) Date: May 26, 2010

(87) PCT Pub. No.: WO2009/069159
PCT Pub. Date: Jun. 4, 2009

(65) Prior Publication Data
US 2010/0303587 A1   Dec. 2, 2010

(51) Int. Cl.
*H02P 23/12* (2006.01)
(52) U.S. Cl.
USPC ............... 318/400.14; 355/272; 414/222.01

(58) Field of Classification Search
USPC .......... 414/222.01; 318/400.01, 700, 400.14, 318/721, 779, 799; 335/153, 222, 272
See application file for complete search history.

(56) References Cited

U.S. PATENT DOCUMENTS

| 4,398,167 A | 8/1983 | Dickie et al. |
| 7,764,030 B2 * | 7/2010 | Miyajima et al. ........ 318/400.04 |

FOREIGN PATENT DOCUMENTS

| EP | 592083 A1 * | 4/1994 |
| EP | 1 067 657 A1 | 1/2001 |
| EP | 1 728 7499 A2 | 12/2006 |
| JP | 2-74143 A | 3/1990 |
| JP | 11-136922 A | 5/1999 |
| JP | 2002-300766 | 10/2002 |
| JP | 2003-79124 A | 3/2003 |
| WO | WO 2005/071817 A1 | 8/2005 |
| WO | WO 2007/122359 A1 | 11/2007 |

* cited by examiner

*Primary Examiner* — Joshua Rudawitz
(74) *Attorney, Agent, or Firm* — Birch, Stewart, Kolasch & Birch, LLP

(57) ABSTRACT

The invention is an operating device including an apparatus suited to move a support with an alternating motion around an axis. The apparatus includes one or more permanent magnets arranged along a section of a circumference that is concentric with the axis and a winding controlled by a control unit. The invention also concerns a machine for checking and inspecting containers.

24 Claims, 9 Drawing Sheets

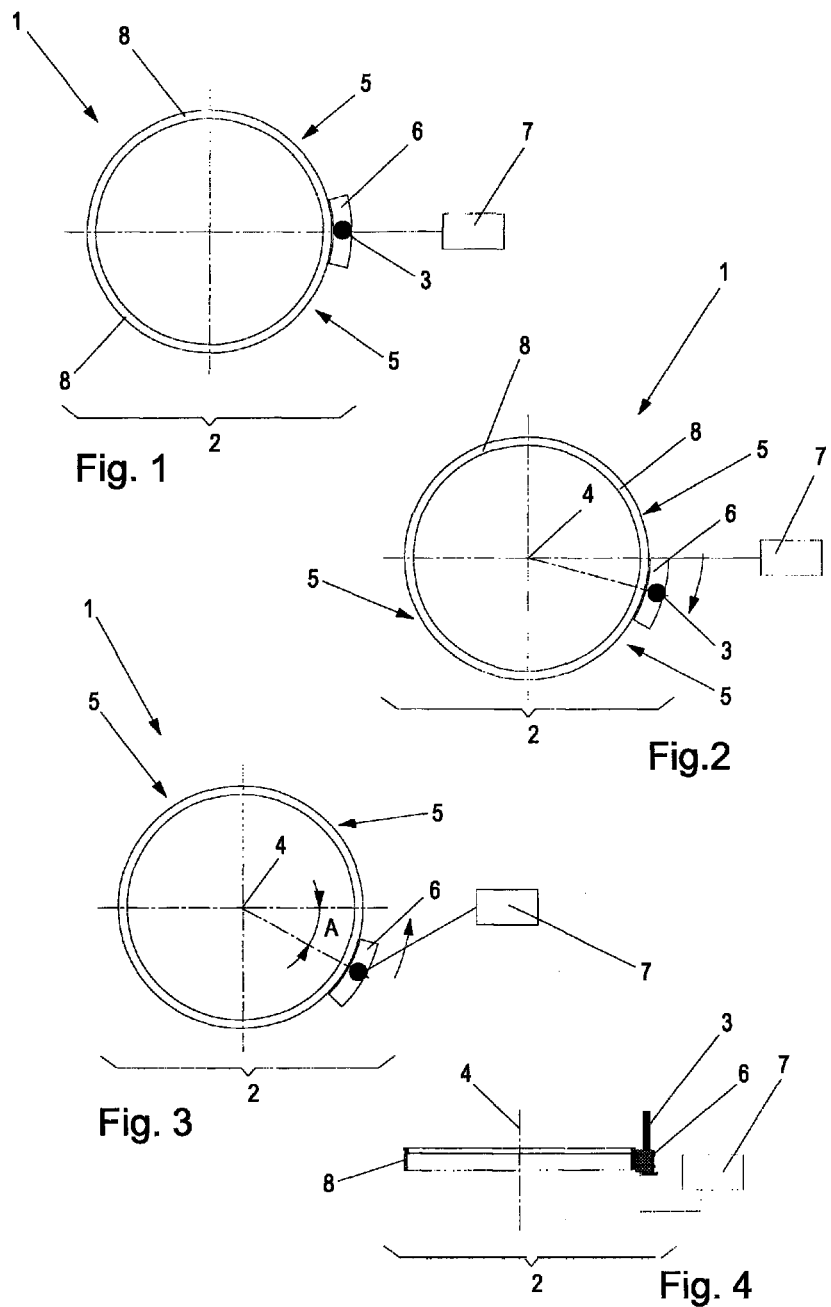

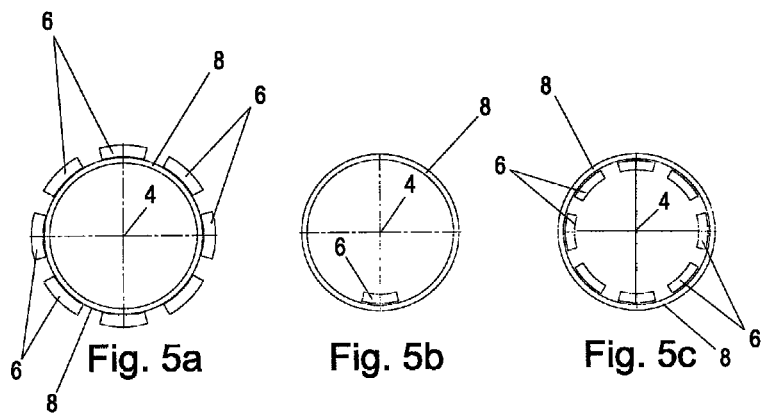
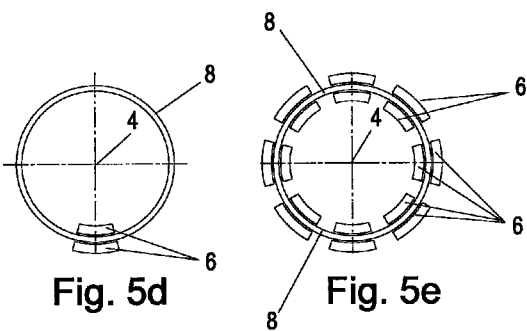
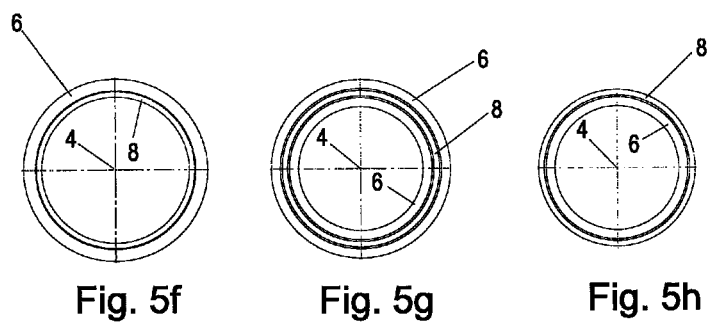
Fig. 5a  Fig. 5b  Fig. 5c
Fig. 5d  Fig. 5e
Fig. 5f  Fig. 5g  Fig. 5h

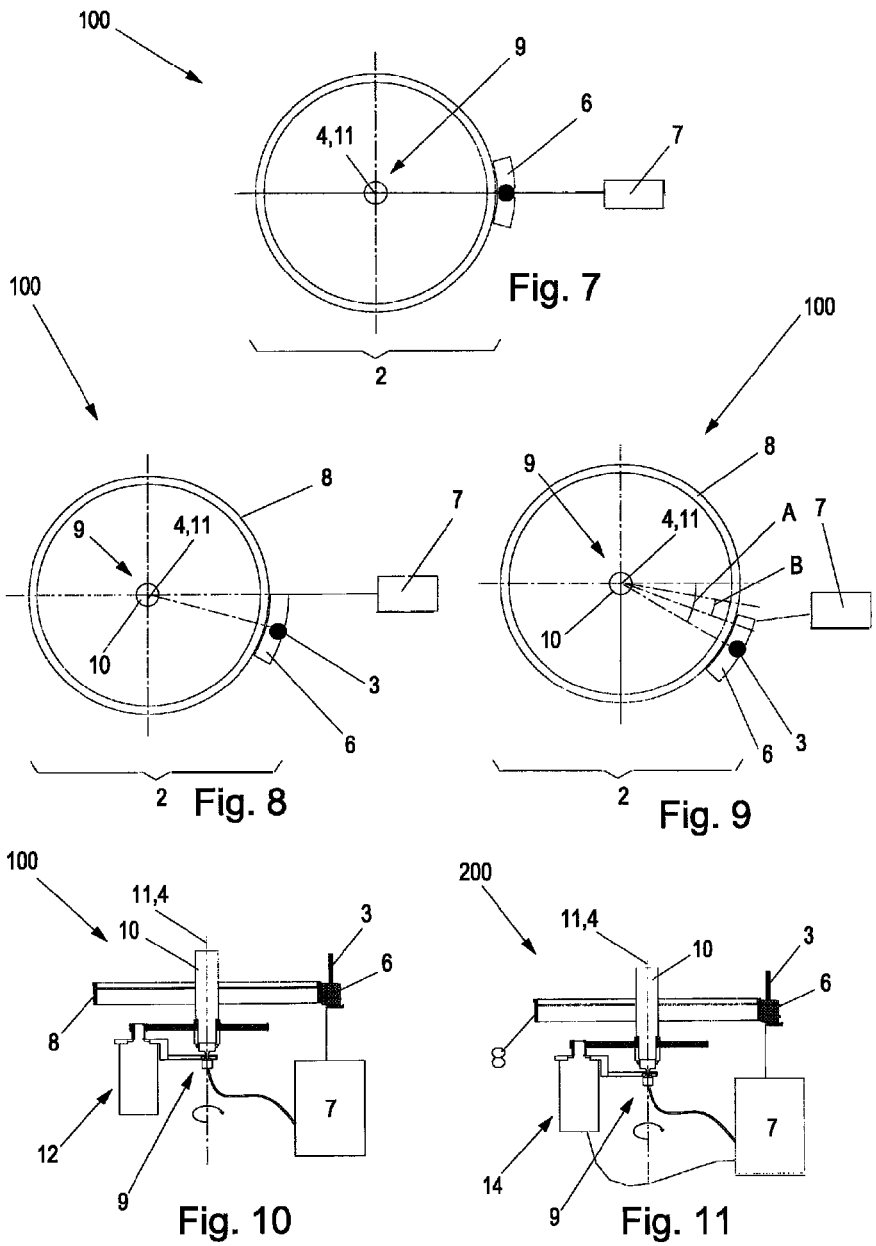

OPERATING DEVICE PREFERABLY FOR MACHINES FOR CONTROLLING AND INSPECTING CONTAINERS AND/OR THEIR CONTENTS, AND CORRESPONDING MACHINE

The invention concerns an operating device to be used preferably in machines for controlling and inspecting containers, and a corresponding inspection machine. More particularly, the invention concerns a synchronisation device to be used in machines for controlling and inspecting containers and/or their contents, preferably in the pharmaceutical sector, and a corresponding machine.

As already known, some products are packed and sealed in containers.

In particular in the pharmaceutical sector, some products are placed in containers and sealed therein, said containers being for example bottles or vials made of glass or a synthetic material, like for example plastic, or similar materials. Said containers, once sealed and sent out of the filling and sealing system, are subjected to various inspections and checks.

These checks make it possible to identify, for example, any foreign particles inside the containers and/or their contents and/or defects in the closure of the containers and/or in the cap, cracks, flaws and/or to record the chemical-physical characteristics of the material contained in the containers.

These checks and inspections concern more generally the conditions of the container and/or of the product contained therein. It is also clear that the container can be checked even before filling it.

Said checks are carried out with special machines that allow this operation to be performed while the container is moving along the production line.

More particularly, the machines or systems of known type generally comprise:
- a loading unit for the containers to be checked;
- rotary support means consisting of a cylinder, also called carousel, radially provided with a plurality of seats arranged side by side, each suited to receive one container to be checked from the loading unit;
- means for recording the characteristics of the container to be checked, arranged on the perimeter of the cylinder and facing said seats;
- an operating or synchronisation device suited to maintain a relative angular speed equal to zero between the bottle positioned on the rotary support and the recording means, said device being suited to maintain said relative speed equal to zero for the period of time necessary for recording the characteristics to be checked;
- an unloading unit for the checked containers, suited to collect the checked containers from the rotary support in order to convey them out of the system or to recirculate them.

It is important to notice that in order to perform the above mentioned recording operations correctly it is necessary to keep the bottle still with respect to the recording means for the time required to record the parameter to be checked.

The known synchronisation devices, also called mechanical oscillators, are mechanical and are suited to transform an incoming continuous rotary motion into a reduced continuous rotary motion on an outlet shaft and into an alternating motion of a support.

More precisely, said devices comprise a rotary shaft driven by an electric motor that, through a mechanical system of gears and cams, rotates a pin to which the cylinder is secured and at the same time moves with an alternating motion a moving support to which the recording means are fixed.

More particularly, the above mentioned mechanical system with conjugate cams and roller feeler ensures that the moving support moves along an arc of a circle and maintains for a given interval of time a relative speed equal to zero with respect to the rotating pin. In other words, the mechanical system ensures that for a given amplitude of an arc of a circle of the trajectory of the cylinder the angular speeds of the cursor and of the moving support are the same.

The laws of motion and the amplitude of the oscillations of the moving support are determined by the profile of the cams.

A first drawback posed by the mechanical synchronisation devices of known type used in the systems for checking pharmaceutical products in particular lies in that these devices are complex, heavy and bulky.

Another drawback lies in that the presence of kinematic motions in the devices mentioned above gives origin to mechanical slacks and therefore makes it difficult to manage the movement of the sensors precisely and in a repetitive manner.

A further drawback lies in that the mechanical parts of these mechanical synchronisation devices generate friction and are therefore subject to wear, which considerably reduces the operating life of the mechanical parts themselves and therefore of the devices that comprise them.

A further drawback is represented by the fact that the mechanical synchronisation devices need lubrication.

Another drawback is constituted by the fact that the above mentioned friction generates a power loss that is all but negligible.

Another drawback lies in that the speeds and accelerations that can be reached by the sensors are limited.

Another drawback lies in that the elasticity of the components of mechanical synchronisation devices causes mechanical resonance phenomena and therefore undesired oscillations and vibrations of the sensors even during the recording stage.

A further drawback is represented by the fact that the ratio between the time taken for checking the containers and the time the cylindrical support needs to perform one revolution is fixed, being determined by the transmission ratios between the mechanical parts of the kinematic chain of the synchronisation device that transmits motion to the sensors.

Another drawback lies in that the components of mechanical synchronisation is devices must be constructed with high precision and minimum tolerance values in order to ensure the best possible synchronism between the motion of the support and that of the rotating pin.

A further drawback connected to the preceding one is represented by the fact that mechanical synchronisation devices are expensive.

The object of the present invention is to overcome the drawbacks described above.

In particular, it is a first object of the invention to construct an operating device preferably for machines for controlling and inspecting containers and/or their contents, and a corresponding machine.

It is a further object of the invention to construct a synchronisation device suited in particular to be used in systems or machines for checking and inspecting containers and/or the product contained therein, in the pharmaceutical and food industry, and a corresponding machine.

It is another object of the invention to construct a device and a machine that allow containers and/or their contents to be checked automatically and continuously, without interruption.

It is a further object of the invention to construct a device that has a substantially compact structure and therefore smaller overall dimensions compared to comparable devices of known type.

It is another object of the invention to construct a device and a machine that make it possible to eliminate or at least to minimise the use of mechanical transmission members for moving the sensors that check the containers.

It is a further object of the invention to construct a device and a machine characterised by reduced friction and therefore reduced wear and power loss, said device and machine needing less maintenance than analogous devices of known type.

It is a further object of the invention to construct a device that makes it possible to move a support suitable for supporting the sensors that check the containers in a precise and repetitive manner.

It is a further object of the invention to construct a device and a machine that make it possible to obtain high support positioning speeds and therefore high sensor speeds.

A further object of the invention is to construct a machine that, compared to equivalent machines of known type, allows a larger number of containers to be checked per unit of time.

It is a further object of the invention to construct a device and a machine that are efficient and reliable.

It is another, yet not the least object of the invention to construct a device that is light, simple from the point of view of design and execution, economic and easy to construct and to assemble.

The objects described above are achieved by an operating device and a corresponding machine described and characterised in the respective independent claims.

Advantageous embodiments of the invention are the subject of the dependent claims.

A particular embodiment of the proposed solution advantageously makes it possible to construct a device and a machine in which it is possible to vary at will the frequency and/or the amplitude with which the moving support moves with alternating motion per each revolution of the rotating pin, and therefore of the recording means, in a practical and immediate way.

Still advantageously, the proposed solution makes it possible to construct a device and a machine on which it is possible to intervene in order to change the ratio between the time necessary for checking the containers and the time taken by each revolution of the carousel.

Still advantageously, the proposed solution makes it possible to carry out a device in which maintenance operations for replacement of any faulty components are easier than those required for analogous devices of known type.

The aims and advantages described above will be highlighted in greater detail in the descriptions of some preferred embodiments of the invention, supplied as examples without limitation, with reference to the attached drawings, wherein:

each of Figures from 1 to 3 shows a schematic and plan view of the device of the invention, in the same number of operating positions;

FIG. 4 shows a schematic lateral view, partially sectioned, of the device shown in FIG. 1;

each of Figures from 5a to 5h shows a schematic plan view of the same number of variants of some components of the device shown in FIG. 1;

each of Figures from 6a to 6p shows a section view of the same number of variants of some components of the device of the invention;

each of Figures from 7 to 9 shows a plan view of another example of a device carried out according to the invention;

FIG. 10 shows a schematic lateral view, partially sectioned, of the device shown in FIG. 7;

FIG. 11 shows a schematic lateral view, partially sectioned, of another example of the device carried out according to the invention;

Figure 12:
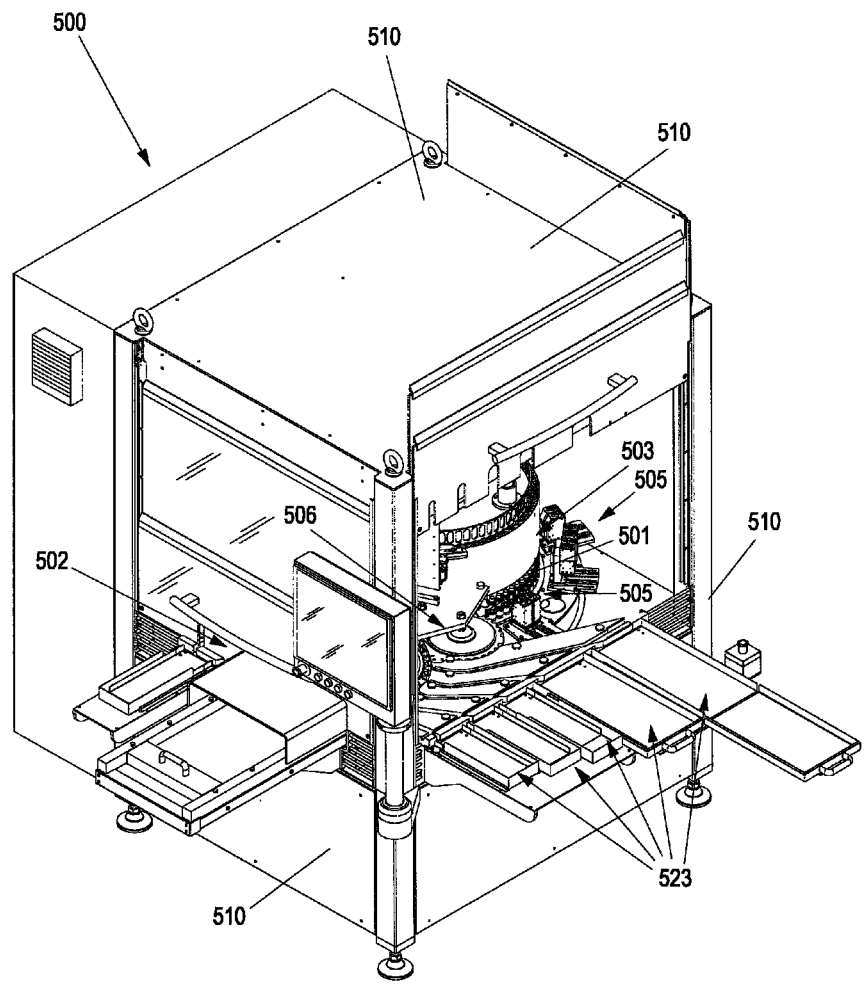
FIG. 12 shows a perspective view of a machine or system that is also the subject of the invention.

each of Figures from 19 to 24 shows a plan view of some parts of the machine shown in FIG. 12, each figure illustrating a different operating position.

First of all it is important to point out that corresponding components in different examples of embodiments are indicated by the same reference numbers.

The position indications given in the different examples of embodiment should be transferred to the new position.

While the following description, made with reference to the above mentioned figures, illustrates some particular embodiments of the present invention, it is clear that the invention is not limited to said particular embodiments, rather, the individual embodiments described here below clarify different aspects of the present invention, the scope and purpose of which are defined in the claims.

Some examples of embodiment of the invention described below refer to a system for checking and inspecting a plurality of containers and/or the product contained therein. More particularly, the system described is a system for checking containers containing pharmaceutical products that uses an operating device carried out according to the invention.

It is clear, however, that the proposed solution can be applied to any machine or system where part of the same machine or system must perform a particular forward-backward movement, or so-called alternating movement, preferably around a rotation centre, for example in order to follow and check a series of containers guided on a transport line.

An operating device carried out according to the invention is represented in Figures from 1 to 4, where it is indicated as a whole by 1.

It comprises means, indicated as a whole by 2, suited to move at least one support 3, also called cursor, with an alternating motion around a first axis 4.

According to the invention, the means 2 comprise one or more permanent magnets 5 arranged along at least one section of a circular trajectory that is concentric with the axis 4, and at least one winding 6, said winding 6 being controlled by a control unit 7.

More generally, the operating device 1 comprises at least two parts that are set moving with a reciprocal motion to obtain a controlled oscillation around the axis 4 with any law of motion.

More generally, the magnets are arranged along at least one section of a non rectilinear trajectory, preferably curved and more particularly circular.

In the preferred non-limiting embodiment of the invention illustrated herein, the support or cursor 3 is integral with the winding 6 that can move along a second circular guide, not illustrated, concentric with the guide element 8.

In the particular non-limiting embodiment of the invention illustrated herein, the permanent magnets 5 are arranged on a circular guide element 8.

More precisely, the permanent magnets 5 are arranged side by side with inverted polarity and generate a permanent magnetic field that interacts with the magnetic field generated by the winding 6 when the winding is activated by the control unit 7.

More precisely, the control unit 7, by properly varying the voltage and/or current in the winding 6 (for example varying wave form, frequency and amplitude) also to varies the direction of motion of the support 3.

This makes it possible to obtain the desired forward-backward movement, also called oscillation movement, around the axis 4, schematically shown in Figures from 1 to 3, which can have any amplitude, as will be better illustrated below.

More particularly, in the example shown, the cursor starts from a first position shown in FIG. 1 and reaches a second external position, shown in FIG. 3, to successively return to the position shown in FIG. 1, moving within an angle A visible in FIG. 3.

It should also be observed that, by varying the voltage and current in the winding (for example varying wave form, frequency and amplitude), the same control unit varies the repulsive force between the winding 6 and the permanent magnets 5, thus generating the relative motion between the winding 6 and the magnets 5 with different speeds and allowing variable acceleration and braking intensity to be obtained.

As an alternative, the winding 6 can be fixed and the moving support or cursor 3 can be integral with the circular guide element 8 that in this case will move around the axis 4. In other words, in this variant it is the ring 8 integral with the cursor 3 that moves, while the winding 6 is fixed. This advantageously makes it possible to avoid using, for example, the electric sliding contacts necessary for supplying power to the winding 6, or to avoid mechanical stress on the power supply cables, as well as to reduce the number of moving parts.

It is also clear that the winding 6 and the ring 8 can have any shape, provided that the surfaces in reciprocal motion are coupled.

It is also clear that the winding 6 and the ring 8 can have any size, provided that the surfaces in reciprocal motion are coupled.

The above is valid also if these surfaces degenerate in a point or a line. This occurs, for example, when the winding 6 is a parallelepiped. In this case, in fact, the winding and the circular element 8, having polygonal cross section, are coupled on a line.

If the circular element has circular cross section and the winding 6 is a parallelepiped, the two components are coupled in the area at the minimum distance, that is, on a point.

As regards the control unit 7, it preferably comprises a microprocessor unit.

More particularly, said control unit 7 may comprise a PLC and/or computer and/or microprocessor and/or an electric motor drive and be provided with interface means (not illustrated), comprising for example displays, keyboards, mouses ecc. Said interface means make it possible to set the operating parameters of the device 1.

More particularly, the operator, using the above mentioned interface means, can set the speed of the cursor 3 or the type of motion, for example to make the cursor perform a uniform and/or non-uniform oscillation but with variable accelerations and/or speeds. As an alternative, the operator can determine the time or duration of the forward-backward cycle or the number of cycles per unit of time (frequency) of the forward-backward cycle, or the amplitude of these oscillations, ecc.

Each one of Figures from 5*a* to 5*h* represents a different embodiment of the device described above.

In particular, these embodiments differ from one another due to the number of windings indicated by 6 and to the position assumed by each winding 6 with respect to the element 8 and therefore to the magnets 5.

More particularly, in FIG. 5*a* the device comprises eight windings arranged opposite the outer surface of the circular element.

In FIG. 5*b* the device comprises a single winding arranged inside the circular element.

In FIG. 5*c* the device comprises eight windings that are all arranged opposite the inner surface of the circular element.

In FIG. 5*d* the device comprises a single winding arranged opposite both the inner surface and the outer surface of the ring-shaped element.

In FIG. 5*e* the device comprises eight windings, each arranged opposite both the inner surface and the outer surface of the ring-shaped element.

In FIG. 5*f* the device comprises a single ring-shaped winding arranged opposite the outer surface of the ring-shaped element.

In FIG. 5*g* the device comprises a single ring-shaped winding arranged opposite both the inner and the outer surface of the ring-shaped element.

In FIG. 5*h* the device comprises a single ring-shaped winding arranged exclusively opposite the inner surface of the ring-shaped element provided with permanent magnets.

It is also clear that the element 8 provided with permanent magnets can have a different geometrical shape, provided that it is not rectilinear. More particularly, said element 8 may for example develop on a section of a circumference.

It is also clear that the element 8 provided with permanent magnets 5 and the winding 6 can have different cross sections.

By way of example, Figures from 6*a* to 6*p* show some different cross sections of the winding indicated by 6 and of the support element 8 of the magnets 5.

Figures 6A, 6B, 6C:
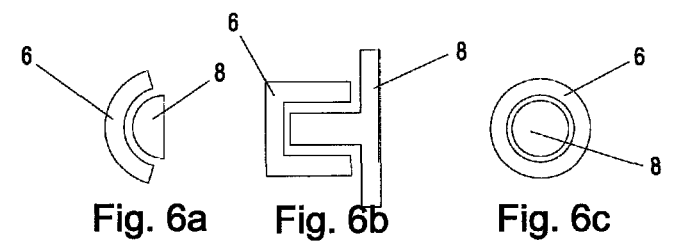
Figures 6D, 6E, 6F:
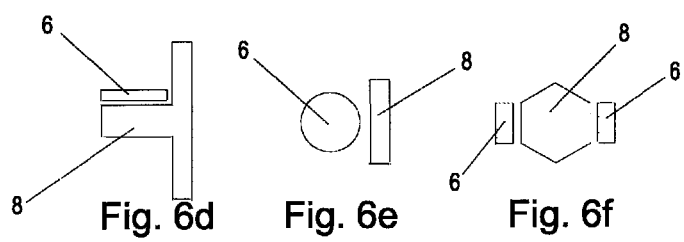
Figures 6G, 6H, 6I:
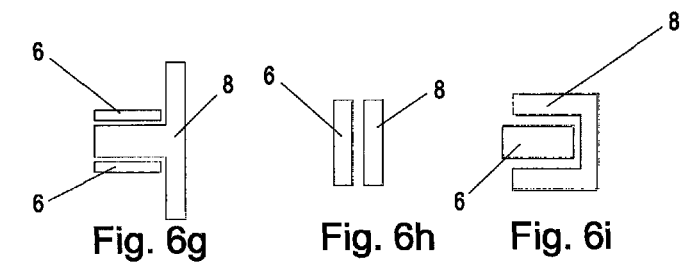
Figures 6L, 6M, 6P:
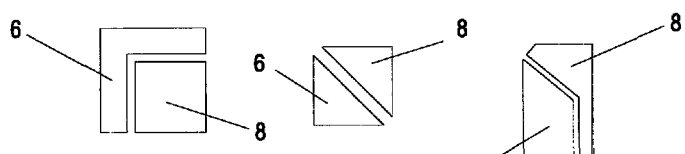
Figures 6N, 6O:
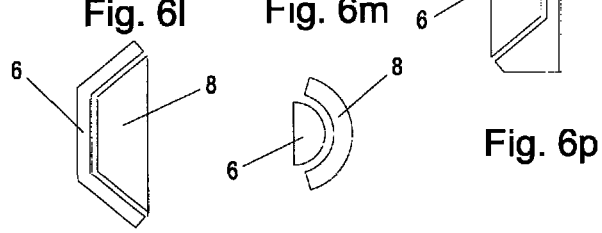

In the above mentioned figures the winding 6 and the element 8 provided with the permanent magnets 5 have mixtilinear section, as in FIG. 6*a*, or 6*o*, or polygonal as in FIGS. 6*b*, 6*d*, 6*e*, 6*f*, 6*g*, 6*h*, 6*i*, 6*l*, 6*m*, 6*n*, 6*p*, or circular as in FIGS. 6*a*, 6*c*, 6*e*, 6*o*, or combinations of these.

It is clear that in other embodiments of the invention the cross sections of the winding and of the support may be inverted with reference to Figures from 6*a* to 6*p*. In other words, with reference to Figures from 6*a* to 6*p*, the geometry of the winding 6 may be that of the element 8 and the section of the element 8 may be that of the winding indicated by 6.

A further construction variant of the device of the invention, indicated as a whole by 100 in the Figures from 7 to 10, differs from the preceding ones due to the fact that the control unit 7 cooperates with means 9 suited to record the rotation speed of a rotating pin 10, in order to control the means 2 in such a way as to maintain a relative speed equal to zero between the support 3 and the rotating pin 10 for a given interval of time.

In other words, the control unit 7 acts on the means 2 in such a way as to ensure that the support element 3 moves with an alternating motion, maintaining the same angular speed for the cursor and the support for a given angle B.

It is clear that both the angle A and the angle B can be set by the operator through the control unit 7.

It should also be noted that in the particular non-limiting embodiment represented herein, the first axis 4 and the second axis 11, besides being parallel to each other, coincide with the axis of the pin 10. More precisely, in the example shown they are all coincident.

As regards the means 9 suited to record the rotation speed of a rotating pin, they comprise a transducer, preferably consisting of an encoder or a speedometer dynamo.

As regards the rotating pin 10, it is set rotating by power means 12 comprising, in the non-limiting example illustrated herein, a gear motor unit including an electric motor.

A further construction variant of the device that is the subject of the invention, indicated as a whole by 200 in FIG. 11, differs from the previous ones due to the fact that it also comprises second means 14 controlled by the control unit 7, said second means being suited to move the pin 10 with a rotary motion with respect to the second axis 11.

In this case, to advantage, the control unit 7 acts simultaneously both on the means that move the pin 10 and on the means that move the cursor, thus guaranteeing further and greater precision in the control and synchronisation of the two movements, rotary (of the pin 10) and oscillating (of the support 3).

It should be noted, also in this case, that the first and second axis 4 are parallel to each other. More precisely, in the example illustrated herein they are coincident.

It is clear that in other embodiments of the invention they may be parallel but not coincident.

As regards the second means 14, they preferably comprise an electric motor controlled by the control unit 7, provided with a shaft with a system of kinematic motions suited to set the pin 10 rotating. These kinematic motion systems generally comprise a mechanical gear motor.

FIG. 12 shows a preferred but non-limiting embodiment of a system or machine for checking and inspecting containers and/or their contents, indicated as a whole by 500, which is also the subject of the present invention.

The machine, indicated as a whole by numeral 500, is suited to verify the conditions and the contents of the containers 501 containing, for example, a pharmaceutical product. It is provided, as will be better explained below, with an operating device of the type described above.

Figure 13:
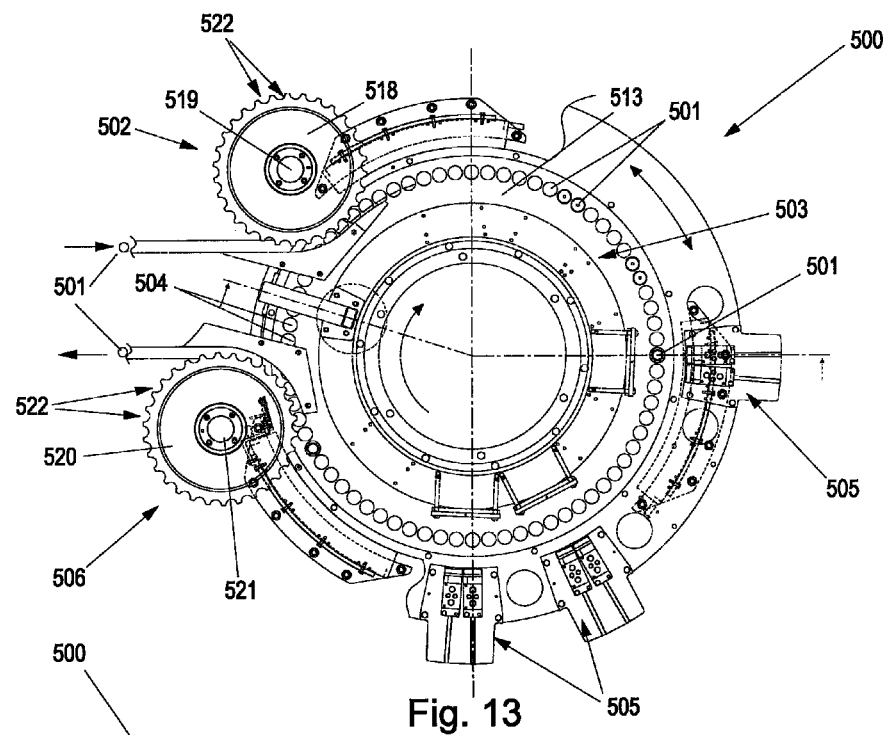
FIG. 13 shows a plan view of some parts of the machine or system shown in FIG. 12.
Figure 14:
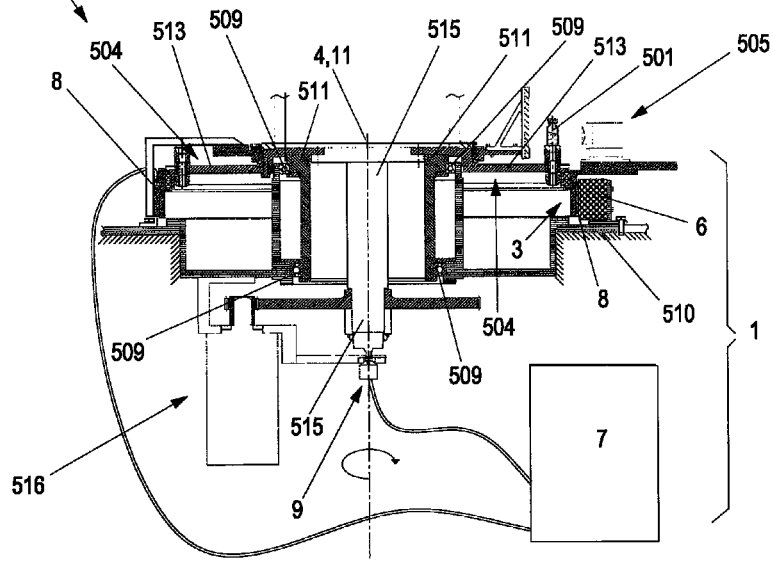
FIG. 14 is a cross-section view of the machine or system shown in FIG. 12.
Figure 15:
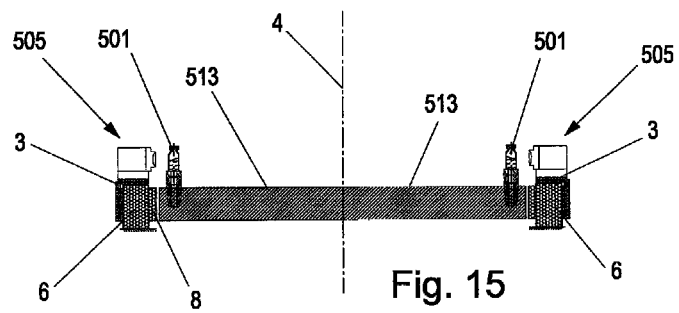
FIG. 15 is a cross-section view of some parts of the machine or system shown in FIG. 12.

More particularly, the machine 500 comprises, as shown in detail in FIG. 13:
- a loading unit for the containers to be checked, indicated as a whole by 502;
- rotatable support means 503 provided with a plurality of seats 504 positioned side by side, each suited to receive from the loading unit 502 a container 501 to be checked;
- means 505 for recording the characteristics to be checked of the container 501, facing at least one of the above mentioned seats 504;
- an operating device 1, better visible in FIG. 14, suited to maintain a relative speed equal to zero between the container 501 positioned on the support 503 when this is rotating and the recording means 505, said device 1 being suited to maintain said relative speed equal to zero for a time interval and/or an angle necessary for recording the characteristics of the bottle 501 to be checked;
- an unloading unit 506 for the checked containers 501, suited to collect the checked containers from the rotating support 503 in order to convey them out of the machine or to recirculate them.

The operating device 1 is suited to maintain the same angular speed for both the support means 504 rotating around an axis 11 and for the recording means 505 that move with an alternating motion around the axis 4.

More particularly, said angular speed is kept constant for an angle that can be set by the operator and is such as to ensure the correct measurement of the parameters to be checked by the recording means 505.

According to the invention, the operating device consists of one of the operating devices described above.

More particularly, in the preferred embodiment of the invention represented herein, said means comprise the winding 6 integral with the frame 510 of the system and the support element 3 of the permanent magnets constituted by a ring-shaped element 8.

The support element 3 is constituted, in the example, by a ring-shaped element that is rotatably coupled, by means of bearings 509, to a pin 511 fixed to the frame 510. The recording means 505 are integral with the element 3.

Figure 16:
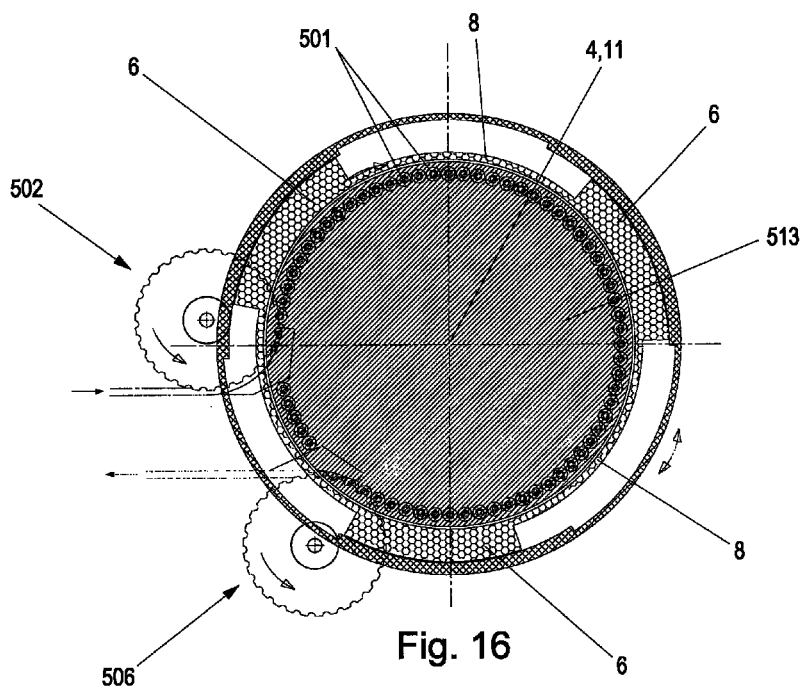
FIG. 16 shows a plan sectional view, along a horizontal plane, of some parts of the machine or system shown in FIG. 12.

As regards the rotating support means 504, they preferably comprise a cylinder 513, or first disc, also called carousel, radially provided with a plurality of seats 504, visible in FIG. 13, positioned side by side, each suited to receive from the loading unit 502 a container 501 to be checked, as can be seen also in FIG. 16. These means 504 also comprise pressing devices, not illustrated herein, suited to press the container 501 against the wall of the seat 504.

Said cylinder 513 is integral with a rotating pin 515 and is moved by the power means 516 consisting of a gear motor unit comprising an electric motor. In the preferred embodiment of the invention illustrated herein, the means 516 are not controlled by the control unit 7.

The recording means 505 are arranged along the perimeter of the cylinder 513 and, as explained above, they face the above mentioned seats 504, as shown also in FIG. 16.

Said recording means 505 are constituted by sensors.

In the non-limiting example of embodiment illustrated herein, said sensors comprise optical sensors, more precisely cameras.

It is clear, however, that these sensors can be of any type, for example temperature sensors or other types of sensors and can employ different technologies, for example ultrasound technology.

As to the loading unit 502, it substantially comprises a second disc 518 rotatably coupled to a corresponding pin 519 called loading star wheel, and the unloading unit 506 comprises a third disc 520, called unloading star wheel, rotatingly coupled to a corresponding pin 521.

Both the second and the third disc 518 and 520 are provided with a plurality of seats 522 arranged side by side, each suited to receive a bottle 501.

More particularly, the second disc 518 is suited to receive the containers 501 coming from an inlet transport unit not illustrated herein and to fit them in the seats 504 of the carousel 513.

The third disc 520 is suited to take the containers (so-called bottles) 501 from the carousel 510 and to deposit them on at least one transporting and sorting unit, provided with several unloading channels 523 visible in FIG. 12.

More precisely, suitable actuator devices make it possible to convey the containers 501 towards different unloading channels 523 according to the parameters recorded by the sensors.

Figures 17, 18:
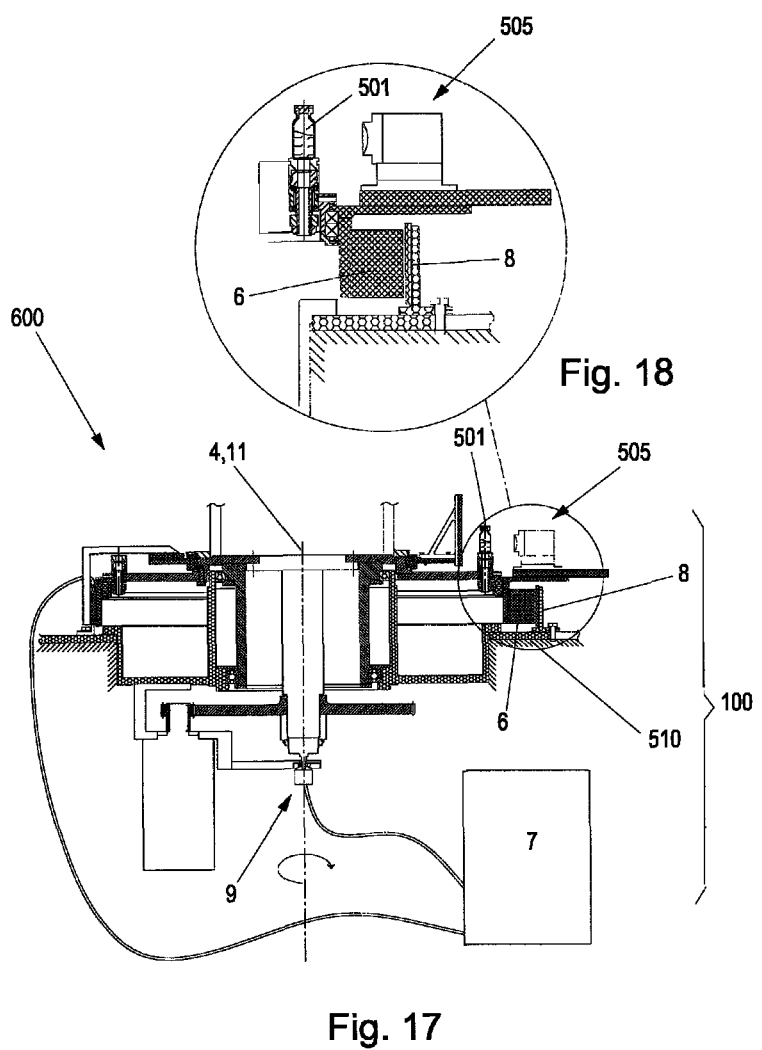
FIG. 17 shows a lateral view of a cross section of another example of a machine carried out according to the invention.
FIG. 18 shows an enlarged detail of some parts of the machine shown in FIG. 17.
Figures 19, 20, 21:
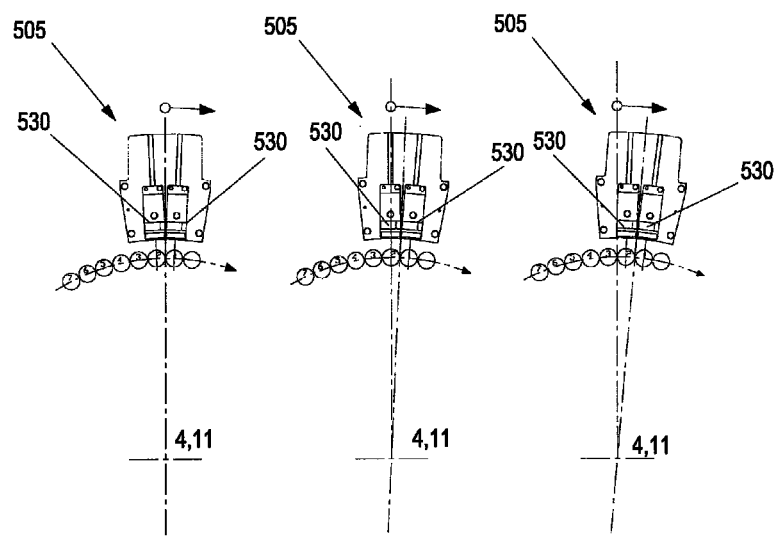

FIGS. 18 and 19 show another embodiment of a machine constructed according to the invention, indicated as a whole by 600.

Said machine 600 differs from the previous ones owing to the fact that the element 8 is integral with the frame 510 and the winding 6 moves with respect to the axis 4 and supports the recording means 505.

In practice, according to the designed operation of the system, the containers guided by the powered transport unit are introduced in the seats, arranged radially on the second disc 518 that is set rotating, and are successively transferred to the seats 504 in the carousel for inspection.

After reaching that position, the container 501 keeps rotating around the axis 4, 11, and after the check it arrives at the level of the unloading unit 506, where it is collected by said unloading unit 506 and conveyed to one of the outlets according to the characteristics recorded.

When the bottle to be inspected arrives near the recording means 505, the control unit 7 activates the winding 6 that generates a magnetic field and moves the recording means 505, accelerating them until reaching the same angular speed as that of the carousel, as shown in FIGS. 19 and 20.

The control unit 7 then maintains the angular speed reached by the cursor 3, and to therefore by the recording means 505, constant for the time or angle set, thus allowing the parameters of the bottle to be checked.

Figures 22, 23, 24:
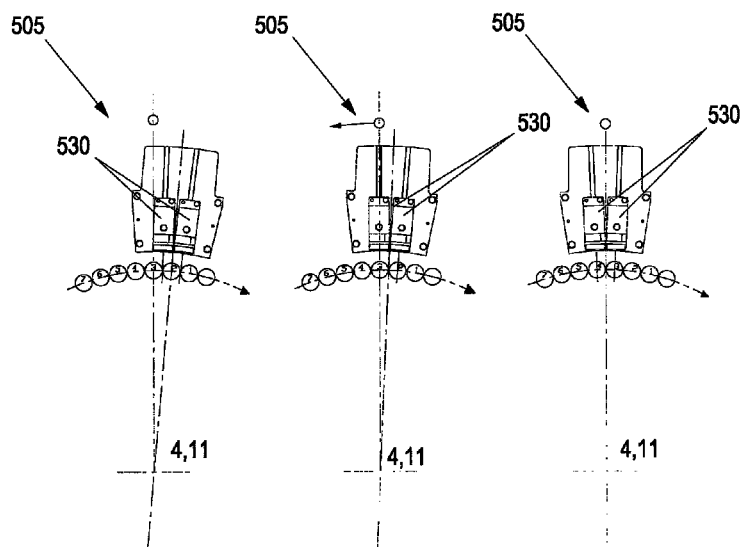

Once the check has been carried out, the control unit decelerates the cursor until stopping it, as shown in FIGS. 21 and 22, successively inverting the direction of motion, as shown in FIG. 23, and bringing the recording means back to the initial position, as shown in FIG. 24.

It should be noted that in the example shown the recording means are constituted by three pairs of cameras 530 that thus allow six containers to be checked per forward-backward cycle.

In other words, the check of the containers positioned on the carousel is carried out automatically by means of the one or more sensors that follow the bottle along a section of revolution of the carousel, thus guaranteeing that in this section the relative speed between the bottle and the sensors is equal to zero.

At the end of this section, the sensors decelerate until their speed equals zero and then invert their direction and return to the starting point, ready to accelerate again and reach and be aligned with the successive container in order to check it.

Once checked, the containers complying with the set parameters proceed to a transporting and sorting unit, otherwise they are rejected or recirculated.

It is clear that in the system that is the subject of the invention the operating device may also not control directly the power means that move the carousel. In this case the operating device (so-called synchronisation device) comprises the means 9 for recording the angular speed of the carousel, that, cooperating with the control unit 7, will consequently move the sensors 505 with an alternating motion.

It is clear from the above description that the proposed solution enables the achievement of the previously-stated objects and overcomes the previously-described drawbacks.

Although the invention has been described with reference to the attached drawings, it may undergo modifications in subsequent stages of its implementation that shall all come within the scope of the invention expressed in the following claims and shall consequently be covered by the present patent.

It is also worth noting that where the characteristics mentioned in the following claims are followed by reference signs, these are used merely to facilitate the readability of the claim itself and shall not be seen as limiting its interpretation in any way.

It is important to underline, moreover, that all the components may be replaced by other, technically equivalent parts and that any materials may be used, provided that they are compatible with the intended usage, and the various elements may be of any size, according to need.

The invention claimed is:

1. Operating device (1, 100, 200) comprising means (2) suited to move at least one support (3) with an alternating motion (A) around a first axis (4), wherein said means (2) comprise one or more permanent magnets (5) arranged along at least one section of a circumference that is concentric with said axis (4) and at least one winding (6), said at least one winding (6) being controlled by a control unit (7) wherein said control unit (7) properly varies the voltage and/or current in said at least one winding (6) in order to vary the direction of motion of said at least one support (3) wherein said at least one support is integral either with said at least one winding (6) or with said one or more permanent magnets (5) characterized in that said at least one support (3) is arrangeable around a rotating pin (10), wherein said first axis (4) and the axis (11) of said pin (10) are parallel to each other and coincident, and wherein said pin (10) is set rotating by separate power means (12) and is able to rotate independently from said at least one support (3); in that said device also comprises means (9) suited to record the rotation speed of said rotating pin (10) and cooperating with said control unit (7), and in that said control unit (7) controls said means (2) suited to move said at least one support (3) in such a way as to maintain a relative speed equal to zero between said at least one support (3) and said rotating pin (10) for a given interval of time and/or a given angle (B).

2. Device according to claim 1, characterised in that said one or more permanent magnets (5) are arranged side by side with inverted polarity and generate a permanent magnetic field that interacts with the magnetic field generated by said at least one winding (6) when the winding is activated by said control unit (7).

3. Device according to claim 1, characterised in that said control unit (7) preferably comprises a microprocessor unit and/or a PLC and/or a computer and/or a drive for electric motors.

4. Device according to claim 1, characterised in that said control unit (7) also comprises interface means.

5. Device according to claim 4, characterised in that said interface means comprise a display and/or a keyboard and/or a mouse.

6. Device (100) according to claim 1, characterised in that the amplitude (A) of said oscillation and said angle (B), for which the angular speeds between said at least one support (3) and said rotating pin (10) are the same, can be set through said control unit (7).

7. Device (100) according to claim 1, characterised in that said means (9) suitable for recording the rotation speed of said rotating pin (10) comprise a transducer.

8. Device (100) according to claim 7, characterised in that said transducer comprises an encoder and/or a speedometer dynamo.

9. Device (100) according to claim 1, characterised in that said power means comprise an electric motor.

10. Device (200) according to claim 9, characterised in that said power means are controlled by said control unit (7).

11. Machine (500, 600) for checking and inspecting containers (501) and/or their contents, comprising:
 a loading unit for the containers (502) to be checked;
 rotatable support means (503) provided with a plurality of seats (504), each suited to receive one container (501) to be checked from said loading unit (502);
 means (505) for recording the characteristics of said container (501) to be checked;
 an operating device suited to maintain a relative speed equal to zero between said recording means (505) and said container (501) positioned on said support means (503), when said support means are rotating, said device being suited to maintain said relative speed equal to zero for a period of time and/or angle necessary to record the characteristics of said container (501) to be checked;

an unloading unit (506) suited to collect said checked containers (501) from said rotating support (503) in order to convey them out of said machine or to recirculate them;

characterised in that said operating device is carried out according to claim 1, said at least one support (3) being integral with said recording means (505).

12. Machine according to claim 11, characterised in that said at least one winding (6) is integral with the frame (510) of said machine.

13. Machine according to claim 12, characterised in that said recording means (505) are integral with said one or more permanent magnets (5).

14. Machine according to claim 13, characterised in that said at least one support element (3) of said permanent magnets (5) comprises a ring-shaped element (8) rotatably coupled to a pin (511) fixed to the frame (510) of said machine by means of bearings (509).

15. Machine according to claim 11, characterised in that said recording means (505) are integral with said at least one winding (6).

16. Machine according to claim 11, characterised in that said rotary support means (504) preferably comprise a cylinder (513) radially provided with said seats (504) positioned side by side.

17. Machine according to claim 16, characterised in that said cylinder (513) is integral with a rotating pin (515) and is driven by the power means (516).

18. Machine according to claim 17, characterised in that said power means comprise a gear motor unit comprising an electric motor.

19. Machine according to claim 11, characterised in that said recording means (505) are arranged along the perimeter of said support means (513), facing said seats (504).

20. Machine according to claim 11, characterised in that said recording means (515) consist of sensors.

21. Machine according to claim 20, characterised in that said sensors are of the optical type and/or ultrasound sensors.

22. Machine according to claim 11, characterised in that said loading unit (502) comprises a second disc (518) rotatably coupled to a corresponding pin (519) and provided with a plurality of seats positioned side by side.

23. Machine according to claim 11, characterised in that said unloading unit (506) comprises a third disc (520) rotatably coupled to a corresponding pin (521) and provided with a plurality of seats positioned side by side.

24. Machine according to claim 11, characterised in that said means (9) suitable for recording the rotation speed of a rotating pin (10) of said device record the rotation speed of said rotatable support means (503).

* * * * *